US010351662B2

(12) United States Patent
Qin et al.

(10) Patent No.: US 10,351,662 B2
(45) **Date of Patent: *Jul. 16, 2019**

(54) DEGRADABLE HYDRAZONE CURING AGENTS AND APPLICATIONS THEREOF

(71) Applicant: ADESSO ADVANCED MATERIALS WUHU CO., LTD., Wuhu (CN)

(72) Inventors: Bing Qin, Shanghai (CN); Xin Li, Cambridge (GB); Bo Liang, Plainsboro, NJ (US)

(73) Assignee: Adesso Advanced Materials Wuhu Co., Ltd., Wuhu (CN)

( * ) Notice: Subject to any disclaimer, the term of this patent is extended or adjusted under 35 U.S.C. 154(b) by 32 days.

This patent is subject to a terminal disclaimer.

(21) Appl. No.: 15/080,317

(22) Filed: Mar. 24, 2016

(65) Prior Publication Data

US 2016/0229949 A1 Aug. 11, 2016

Related U.S. Application Data

(62) Division of application No. 15/024,174, filed as application No. PCT/CN2014/087256 on Sep. 24, 2014.

(51) Int. Cl.

| | |
|---|---|
| ***C07C 251/76*** | (2006.01) |
| ***C08G 59/40*** | (2006.01) |
| ***C07C 251/84*** | (2006.01) |
| ***C07C 251/86*** | (2006.01) |
| ***C08G 59/50*** | (2006.01) |
| ***C07C 317/32*** | (2006.01) |
| ***C08J 5/04*** | (2006.01) |
| ***C08J 5/24*** | (2006.01) |
| ***C08J 11/16*** | (2006.01) |
| ***C09D 163/00*** | (2006.01) |
| ***C08J 11/24*** | (2006.01) |
| ***C08G 59/24*** | (2006.01) |

(52) U.S. Cl.

CPC ........ *C08G 59/4014* (2013.01); *C07C 251/76* (2013.01); *C07C 251/84* (2013.01); *C07C 251/86* (2013.01); *C07C 317/32* (2013.01); *C08G 59/245* (2013.01); *C08G 59/4064* (2013.01); *C08G 59/50* (2013.01); *C08G 59/5046* (2013.01); *C08J 5/042* (2013.01); *C08J 5/24* (2013.01); *C08J 11/16* (2013.01); *C08J 11/24* (2013.01); *C09D 163/00* (2013.01); *C08J 2363/02* (2013.01)

(58) Field of Classification Search

CPC ... C07C 251/76; C07C 251/84; C07C 251/86; C07C 317/32; C08G 59/4014; C08G 59/50; C08G 59/5046; C08G 59/245; C08G 59/4064; C08J 5/042; C08J 5/24; C08J 11/16; C08J 11/24; C08J 2363/02; C09D 163/00

USPC .......................................................... 523/400

See application file for complete search history.

(56) References Cited

U.S. PATENT DOCUMENTS

| | | | | |
|---|---|---|---|---|
| 3,810,889 | A | 5/1974 | Model et al. | |
| 3,849,450 | A | 11/1974 | O'Rear et al. | |
| 4,163,098 | A | 7/1979 | Zondler et al. | |
| 4,210,565 | A | 7/1980 | Emmons | |
| 5,445,854 | A | 8/1995 | Newsham et al. | |
| 2012/0021223 | A1* | 1/2012 | Griffiths | C07C 311/49 428/407 |

FOREIGN PATENT DOCUMENTS

| | | | | |
|---|---|---|---|---|
| CN | 101558106 A | | 10/2009 | |
| CN | 103154153 A | | 6/2013 | |
| CN | 103254407 A | | 8/2013 | |
| CN | 103261300 A | | 8/2013 | |
| CN | 103483554 A | | 1/2014 | |
| JP | 02123125 A | * | 5/1990 | C08G 59/54 |
| JP | 2013060386 A | | 4/2013 | |

OTHER PUBLICATIONS

Alici et al., "Synthesis of New Substituted 1,2,4-Triazines from Isonitrosoketones and Terephthalaldehydedihydrazone", Journal of Heterocyclic Chemistry, 2012, vol. 29, p. 576-579 (Year: 2012).*

Troy et al., "Poly(N,N-Diacylhydrazone)s: Polymers Containing Imide and Imine Functions Linked by Nitrogen-Nitrogen Bonds", Journal of Polymer Science: Polymer Letters Edition, 1984, vol. 22, p. 113-118 (Year: 1984).*

Oikawa et al., "Polymers Containing the s-Triazine Ring. II. Synthesis of Poly(s-triazinylenehydrazones)", Journal of Applied Polymer Science, 1971, vo. 15, p. 913-925 (Year: 1971).*

Honjo et al, JP 02-123125 A machine translation in English, May 10, 1990 (Year: 1990).*

* cited by examiner

*Primary Examiner* — David T Karst

(74) *Attorney, Agent, or Firm* — Weisun Rao; Venture Partner, LLC

(57) ABSTRACT

This invention provides, among others, curing agents of Formula II, methods for preparing these curing agents, prepreg materials, degradable cross-linked polymers and reinforced composites made from these curing agents and epoxy resins, and methods for degrading and/or recycling the degradable polymers and reinforced composites.

Formula II $$C\left(A \underset{}{\overset{N-NH_2}{\overset{\|}{C}}}\right)_n B$$

5 Claims, No Drawings

DEGRADABLE HYDRAZONE CURING AGENTS AND APPLICATIONS THEREOF

CROSS-REFERENCE TO RELATED APPLICATIONS

This application is a divisional application of U.S. application Ser. No. 15/024,174, filed on Mar. 23, 2016, as a national phase application of PCT/CN2014/087256 which claims priority to and benefit of Chinese Patent Application No. 201310440092.0, filed on Sep. 24, 2013, the contents of which are incorporated herein by reference in their entireties.

FIELD OF THE INVENTION

This application is in general in the field of epoxy curing agents and applications thereof, and more specifically relates to degradable cyclic acetal, cyclic ketal diamines epoxy curing agents; prepreg materials, polymers, or reinforcing composite materials based thereon; and degradation of the polymers and reinforced composite materials based thereon.

BACKGROUND OF THE INVENTION

Epoxy resins are an important class of thermosetting compounds. They have diverse applications and are widely used in adhesives, structural materials, lacquer, ceramic manufacturing, printed circuit boards, microelectronics packaging, aerospace industry, etc. Epoxy resins usually are hardened or cured by a cross-linking reaction using one of the following three methods. The properties and applications of a cured resin are greatly influenced by the choice of the hardener or the method of curing.

Method 1: An epoxy resin reacts with itself (i.e., homopolymerizes) via a ring-opening polymerization mechanism of the epoxy groups. The self-curing of epoxy resins usually requires an elevated temperature but can be initiated with either a Lewis acid or a Lewis base catalyst (as opposed to a curing agent).

Method 2: An epoxy resin can be cured with a cyclic acid anhydride. The anhydride can react with the epoxy group, pendant hydroxyls, or residual water to form a carboxylate intermediate, which then reacts with the epoxy group, causing a self-perpetuating reaction between the anhydride and the epoxy resin. Catalytic amounts of tertiary amines are commonly used as additives as they facilitate the opening of the anhydride.

Method 3: An epoxy resin reacts with a polyvalent nucleophilic reagent, e.g., a polyamine, at the room temperature. For instance, the ring opening of the epoxy ring with a primary or secondary amine generates a stable C—N bond, which is then cured to form a three dimensional network structure with a high crosslinking density. The epoxy resin can potentially react with potentially every amine group containing an active hydrogen atom, so that, e.g., a simple diamine ($NH_2$—R—$NH_2$) acts as a tetrafunctional cross-linker and reacts with four epoxy groups. Similar to polyamines, polythiol compounds (HS—R—SH) can also react with epoxy groups to form C—S bonds. The reaction of a thiol group with the epoxy group is greatly facilitated by the presence of a catalytic amount of base, such as a tertiary amine, to result in a faster curing process even at the room temperature.

The most common epoxy resin formulations consist of a diepoxide (resin) and a polyamine compound (curing agent or hardener), which form a polymeric network of essentially infinite molecular weight. The combination of "resin" and "curing agent" sometimes is referred to as "after curing (cured) epoxy resin," "after curing (cured) resin", or simply "resin" or "epoxy resin." The widespread utility of such epoxy formulations is due to their excellent processability prior to curing and their excellent post-cure adhesion, mechanical strength, thermal profile, electronic properties, chemical resistance, etc. Furthermore, the high-density, infusible three-dimensional network of epoxies makes it an extremely robust material, resulting in it being the material of choice for many long-term applications. At the same time, this durability makes its removal, recycling and reworkability notoriously difficult, raising concerns about the longevity of epoxy-based materials in the environment. The cross-linking reactions that occur with two convertibly used component epoxies are essentially irreversible. Therefore, the material cannot be easily dissolved, or melted and reshaped without decomposition of the material. The epoxy resin, due to its excellent physical and mechanical properties, electrical insulation, and adhesive performance, is widely used in composite materials, casting parts, electronics, coating, etc. In particular, fiber reinforced epoxy resin composite materials, especially carbon fiber composites, have been widely used in aerospace, automobile, train, ship, wind energy tidal energy, sporting goods and other industries. It has been estimated that by 2015, global composite material production capacity will significantly increase, and exceed 10 million tons. However, how to deal with and recycle the waste of fiber composites has become a worldwide problem that prevents the fiber composite industry's growth, thereby constraining the sustainable development of fiber composites.

By far, the recycling process of fiber composite materials have been roughly reported in the following ways: 1. High temperature thermal degradation (Thermochimica Acta 2007(454): 109-115), which can recycle composite material to obtain clean filler and fiber, but requires high temperature processing and high standard equipment; 2. Fluidized bed (Applied surface science 2008(254): 2588-2593), which requires high temperature processing to recycle and obtain the clean fiber; 3. Supercutical fluid (water (Materials and design 2010(31):999-1002), alcohol (Ind. eng. chem. res. 2010(49): 4535-4541) or carbon dioxide (CN102181071), for degrading epoxy resin system, which is still in the laboratory stage and far from practical industrialization; 4. Use nitric acid (Journal of applied polymer science, 2004 (95): 1912-1916) to degrade the epoxy resin and obtain fiber with clean surface, which has strong corrosion resistance of acid like nitric acid, requires high standard equipment, and results in low operating security, high recycle cost, and difficult post-processing. Generally, these methods have their limitations in varying degrees, existing disadvantages of fiber shortening, performance degradation, environmental pollution, and high recycling cost and so on, therefore, effective and feasible method for the recycling of waste composite materials is still an issue to be addressed in composites field.

SUMMARY OF THE INVENTION

To solve the problems or overcome the deficiencies of the existing technologies, the present invention provides, among others, degradable epoxy curing agents, the polymers and reinforced composite materials derived from those curing agents and epoxy resin, methods for degrading those polymers and reinforced composites. The degradable composites provided by this invention have excellent mechanical properties, and are suitable for a variety of applications in the field of composites. Under specific conditions, the composite material can be degraded, and the matrix degradation products of reinforcing material and epoxy resin can be separated and recovered. Furthermore, the degradation and recovery method of reinforced composite is economic, easy to control and can be proceed under relatively mild reaction conditions.

Accordingly, this present invention provides the following technical solutions.

In one aspect, the present invention provides curing agent comprising a compound of Formula I or a salt thereof:

Formula I

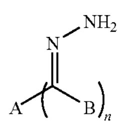

In Formula I:

n is an integer greater than 1;

A is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylen, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-hetero-cycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, arylene-X-arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, heteroarylene-X-heteroarylene, heteroarylene-X-arylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, or alkynylene-heteroarylene-alkynylene;

X is alkylene, alkenylene, oxygen, sulfur, nitrogen, sulfoxide, sulfone, carbonyl, —C(O)O—, —OC(O)O—, —OC(O)NH—, —C(O)NH—, or —HNC(O)NH—;

each B independently is hydrogen, alkyl, cycloalkyl, heterocyclic, heterocycloalkyl, alkenyl, cycloalkenyl, aryl, arylalkyl, heteroaryl, heteroarylalkyl, alkyl-hetero-alkyl, alkyl-hetero-alkenyl, or alkynyl;

or, A and at least one B, together with the carbon atom to which they are bonded, form a saturated or unsaturated ring optionally containing at least one hetero ring atom of O, S, N, or P;

or, at least two B groups, together with A and carbon atoms to which A and B groups are bonded, form a saturated or unsaturated ring optionally containing at least one hetero ring atom of O, S, N, or P.

The ring can be, e.g., 3- to 9-membered (e.g., 3- to 8-, 4- to 8-, 4- to 7-, 5- to 7-, 5- to 6-, or 6- to 7-). An unsaturated ring can be aromatic or non-aromatic.

In some embodiments, n is 2, 3, or 4 in Formula I. In some other embodiments, n is 2 or 3. Of course, n can be 2, 3, 4, 5, 6, 7, or 8, or up to 100 or even higher, as long as a compound with that number for n is chemically possible or feasible.

In some other embodiments, A in Formula I is alkylene, alkylene-hetero-alkylene, alkenylene, alkenylene-hetero-alkenylene, alkylene-hetero-alkenylene, cycloalkylene, heterocycloalkylene, arylene, arylene-X-arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, heteroarylene-X-heteroarylene, heteroarylene-X-arylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, or alkynylene-heteroarylene-alkynylene; and X is alkylene, oxygen, sulfur, nitrogen, sulfoxide (i.e., —SO—), sulfone (i.e., —$SO_2$—), or —OC(O)O—. For example, A can be alkylene, arylene, heteroarylene, arylene-X-arylene, heteroarylene-X-heteroarylene, or heteroarylene-X-arylene. Or, A can be alkylene, arylene, or arylene-X-arylene. Specific examples of A include methylene, ethylene, propylene, phenylene, and phenylene-X-phenylene. Specific examples of X include oxygen, sulfur, nitrogen, sulfoxide, and sulfone. When one terminal of A is not substituted or bonded with any —CB═N—$NH_2$ group, then A in Formula I becomes, e.g., alkyl, alkyl-hetero-alkylene, alkenyl, alkenyl-hetero-alkenylene, alkyl-hetero-alkenylene, aryl, aryl-X-arylene, alkyl-arylene, alkyl-arylene-alkylene, alkenyl-arylene, alkenyl-arylene-alkenylene, alkyl-arylene-alkenylene, alkynyl-arylene, alkynyl-arylene-alkynylene, heteroarylene, heteroarylene-X-heteroarylene, heteroarylene-X-arylene, alkylene-heteroarylene, alkyl-heteroarylene-alkylene, alkenyl-heteroarylene, alkenyl-heteroarylene-alkenylene, alkyl-heteroarylene-alkenylene, alkynyl-heteroarylene, or alkynyl-heteroarylene-alkynylene When A has more than one carbon atoms, the different —CB═N—$NH_2$ groups can be on, or bonded to, the same or different carbon atoms of A. As an example to illustrate the possibility, if A is propylene and n is 2, the two —CB═N—$NH_2$ groups can be both on a same carbon atom of the propylene group, or on different carbon atoms of the propylene group (e.g., 1,3 or 1,2 carbon atoms). Or, if A is ethylene and n is 2, the two In still some other embodiments, each B independently is hydrogen, alkyl, alkyl-hetero-alkyl, alkenyl, alkenyl-hetero-alkenyl, alkenyl-hetero-alkyl, alkyl-hetero-alkenyl, or alkynyl. Particularly, each B independently can be hydrogen or alkyl. When two or more B groups in Formula I are of the same type, e.g., alkyl, they can still be different by having different numbers of carbon atoms or with different substituents.

In yet still some other embodiments, A and at least one B, together with the carbon atom to which they are bonded, form a 3- to 8-membered saturated or unsaturated ring optionally containing at least one hetero ring atom. Examples of the hetero atom include 0, S, N, or P. The ring can be optionally substituted. In this case, the above specific definitions for A and B, when they form a ring, do not apply.

Examples of compounds of Formula I include

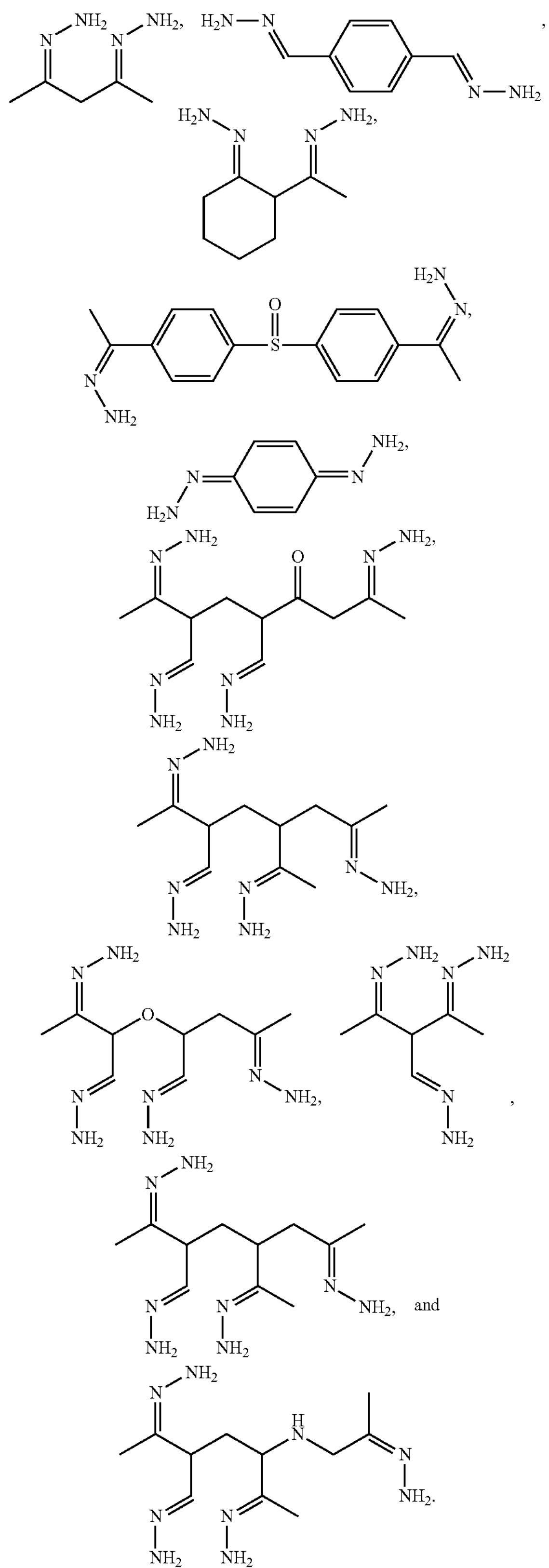

In another aspect, the present invention provides a curing agent comprising a compound of Formula II or a salt thereof:

Formula II

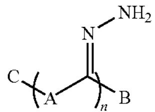

In Formula II, n is an integer greater than 1;

each A independently is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylen, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, or alkynylene-heteroarylene-alkynylene;

B is hydrogen, alkyl, cycloalkyl, heterocyclic, heterocycloalkyl, alkenyl, cycloalkenyl, aryl, heteroaryl, alkyl-hetero-alkyl, alkynyl, or alkyl-hetero-alkynyl; and C is hydrogen, alkyl, cycloalkyl, heterocyclic, heterocycloalkyl, alkenyl, cycloalkenyl, aryl, heteroaryl, alkyl-hetero-alkyl, or alkynyl;

or, C and B, together with A and the carbon atom to which they are bonded respectively, form a saturated or unsaturated ring optionally containing at least one hetero ring atom of 0, S, N or P. The ring can be, e.g., 3- to 9-membered (e.g., 3- to 8-, 4- to 8-, 4- to 7-, 5- to 7-, 5- to 6-, or 6- to 7-). An unsaturated ring can be aromatic or non-aromatic.

In some embodiments, n is 2, 3, or 4 in Formula I. In some other embodiments, n is 2 or 3. Of course, n can be 2, 3, 4, 5, 6, 7, or 8, or up to 100 or even higher, as long as a compound with that number for n is chemically possible or feasible.

In some embodiments, each A independently is alkylene, alkenylene, alkylene-hetero-alkylene, arylene, alkylene-arylene, alkylene-arylene-alkylene, alkenylene-arylene, alkenylene-arylene-alkenylene, alkylene-arylene-alkenylene, alkynylene-heteroarylene, or alkynylene-heteroarylene-alkynylene. When two or more A groups in Formula II are of the same type, e.g., alkyl, they can still be different by having different carbon atoms or with different substituents.

In some other embodiments, each A independently is alkylene or alkenylene.

In still some other embodiments, B is hydrogen, alkyl, cycloalkyl, heterocyclic, heterocycloalkyl, alkenyl, aryl, heteroaryl, alkyl-hetero-alkyl. Specifically, B can be hydrogen, alkyl, or alkenyl.

In yet still some other embodiments, C is hydrogen or alkyl.

In some other embodiments, C and B, together with A and the carbon atom to which they are bonded respectively, form a saturated or unsaturated ring optionally containing at least one hetero ring atom of O, S, N, or P. The ring can be, e.g., 3- to 9-membered (e.g., 3- to 8, 4- to 8-, 4- to 7-, 5- to 7-, or 6- to 7-).

Examples of the compound of Formula II include

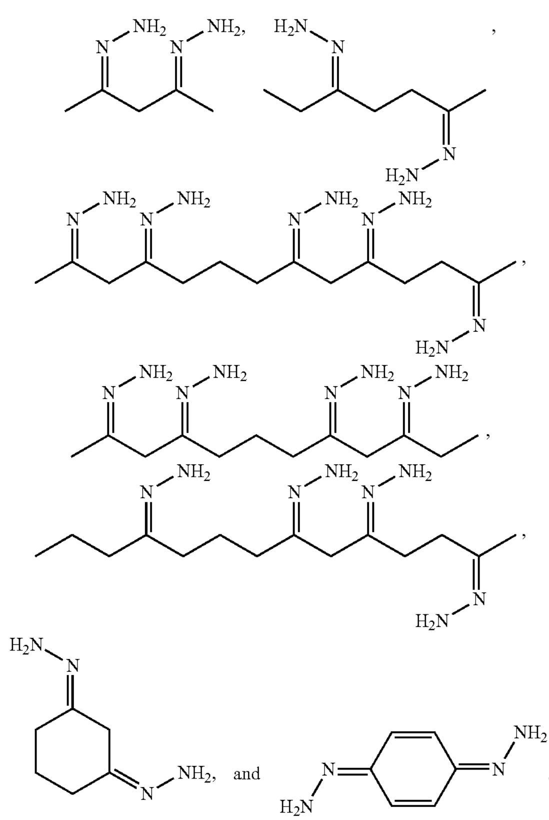

As mentioned above, salts of the compounds of Formula I or II are also within the scope of this invention. To form such a salt, either one or more of the terminal amino groups in each of the compounds or the internal nitrogen atom (i.e., ═N—) can be reacted with an acid, e.g., hydrochloride acid or sulfuric acid, to form a tertiary amine salt. For illustration purpose, examples of such salts include

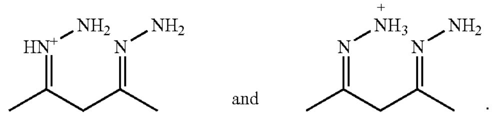

The curing agents described above can be useful for curing an epoxy resin to produce a degradable cured epoxy resin.

Another aspect of the present invention provides a degradable cross-linked polymer comprising a cleavable cross-linking group derived from a curing agent described above and an epoxy resin, wherein at least one amino group in the curing agent is fully reacted to lose both hydrogen atoms and form two bonds with the epoxy resin. As used herein, the term "derived" means that when a curing agent described above containing a compound of Formula I or II cures a polymer, e.g., an epoxy resin, the curing agent would lose at least two active hydrogen atoms of one or two terminal amino groups in the curing agent. For example, one amino group can completely lose its two active hydrogen atoms so that the nitrogen would form to bonds with the cured resin (as shown below in Formulae I-b and II-b as examples), forming the cross-linked polymer. Alternatively, two amino groups can each lose one active hydrogen to form (and derive to) a linking group shown below in Structures I-c and II-c as examples.

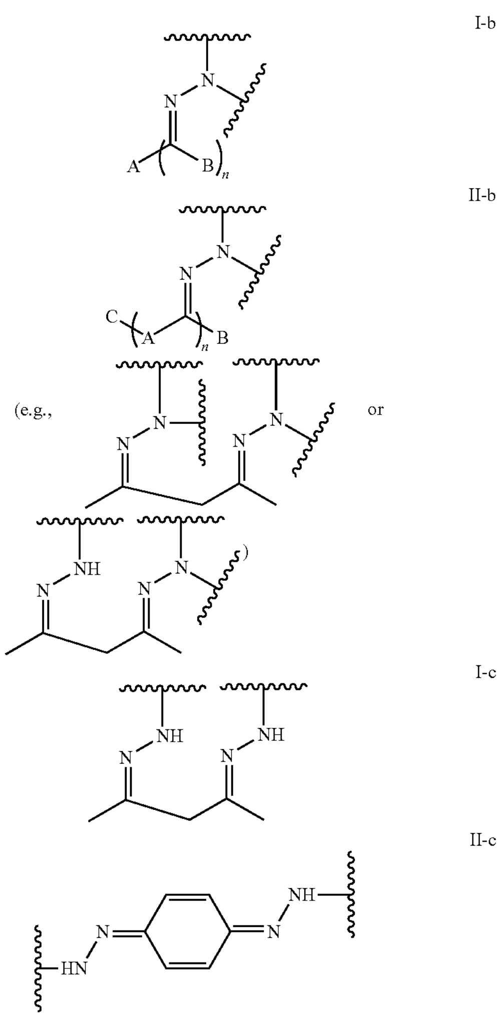

In some embodiments, the epoxy resin comprises a glycidyl ether epoxy resin, glycidyl ester epoxy resin, glycidyl epoxy amine epoxy resin, trifunctional epoxy resin, tetra-functional epoxy resin, novolac epoxy resin, o-cresol form-aldehyde epoxy resin, aliphatic epoxy resin, alicyclic epoxy resin, or nitrogen-containing epoxy resin.

In some other embodiments, the cleavable cross-linking group is derived from

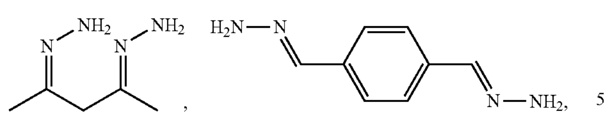

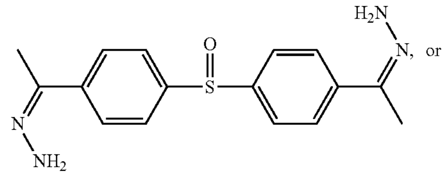

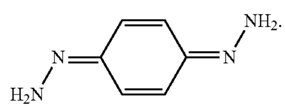

Examples of the cross-linking group include, but are not limited to,

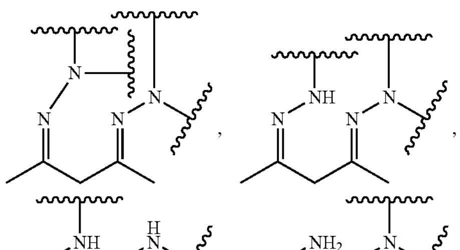

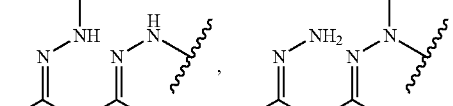

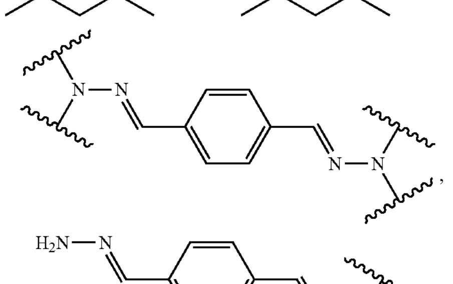

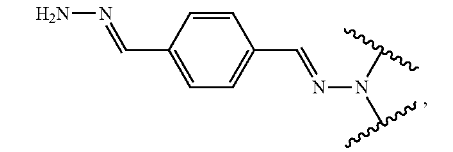

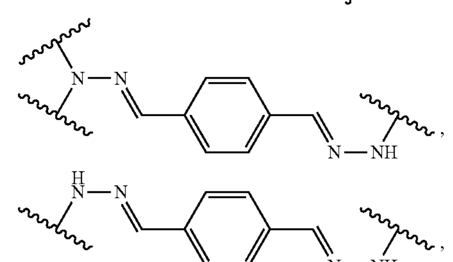

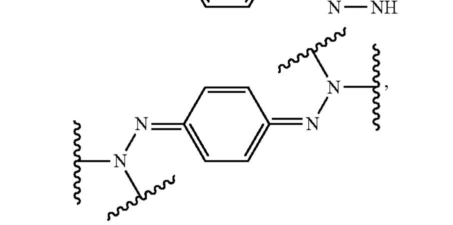

-continued

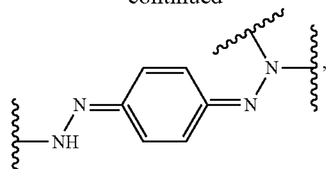

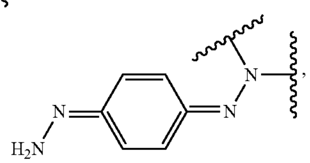

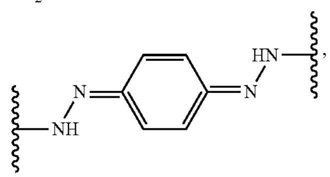

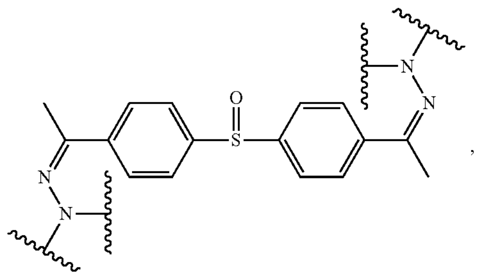

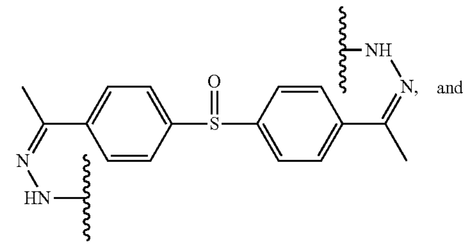

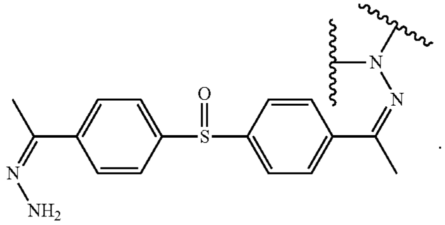

In some examples of the linking group derived from a compound of Formula I or II described above, at least one amino group of the compound is fully reacted to lose both hydrogen atoms; whereas in some other examples, no terminal amino group is required to fully react and lose both active hydrogen atoms.

Another aspect of this invention provides a recyclable prepreg (i.e., pre-impregnated) composition or reinforced composite material, comprising a curing agent as described above, an epoxy resin, an auxiliary material and a reinforcing material. In this recyclable prepreg composition or reinforced composite material, the epoxy resin comprises glycidyl ether epoxy resin, glycidyl ester epoxy resin, glycidyl epoxy amine epoxy resin, trifunctional epoxy resin, tetrafunctional epoxy resin, novolac epoxy resin, o-cresol formaldehyde epoxy resin, aliphatic epoxy resin, alicyclic epoxy resin, or nitrogen-containing epoxy resin; the reinforcing material comprises carbon nanotube, boron nitride nanotube, carbon black, metal nano-particle, metal oxide nanoparticle, organic nanoparticle, iron oxide, glass fiber, carbon fiber, natural fiber, synthetic fiber, or fabrics made therefrom; and the auxiliary material comprises accelerator, diluent, plasticizer, toughening agent, thickening agent, coupling agent, defoamer, flatting agent, ultraviolet absorber, antioxidant, brightener, fluorescent agent, pigment, or filler. For a detailed description of the above-mentioned epoxy resin, please see Epoxy Resins: Chemistry and Technology (Second Ed.). New York: Marcel Dekker Inc. (ISBN 0-8247-7690-9), which is incorporated herein by reference in its entirety.

Still another aspect of this invention provides a method for degrading a degradable cross-linked polymer, a recyclable prepreg composition, or a reinforced composite material described above. This method includes the steps, in the order, of (1) under the heating and stirring conditions, immersing the polymer in a mixed acid and solvent system to obtain a degradation solution; and (2) using an alkaline solution to control the pH of the degradation solution. The method may further include, as an optional step, washing and drying the precipitate and degradation solution after pH adjustment in step (2).

In some embodiments of the methods, the acid comprises a hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid; the alkali comprises lithium hydroxide, sodium hydroxide, potassium hydroxide, calcium hydroxide, sodium carbonate, sodium bicarbonate, potassium carbonate, potassium bicarbonate, or ammonia; each of the solvent for immersing the polymer in step (1) and the solvent for the alkaline solution in step (2) independently comprises methanol, ethanol, ethylene glycol, propanol, isopropanol, butanol, isobutanol, t-butanol, pentanol, hexanol, heptanol, octanol, nonanol, benzyl alcohol, phenethyl alcohol, p-hydroxymethyl benzene, m-hydroxymethyl benzene, o-hydroxy benzene, p-hydroxyethyl benzene, m-hydroxyethyl benzene, o-hydroxyethyl benzene, water, N, N-dimethylformamide, N, N-dimethylacetamide, N-methylpyrrolidone, dimethyl sulfoxide, tetrahydrofuran, methyl tetrahydrofuran, glycerol, or dioxane.

In some other embodiments, the heating temperature is in the range of 80~150° C., and the heating time is 4~8 hours, and the mass concentration of the acid in the solvent system is 0.5~20% (w/w); and in step (2), the temperature is in the range of 5~50° C., the final pH is 6~12, and the mass concentration of the alkali in the solvent is 5~30% (w/w). In still some other embodiments, in step (1), the heating temperature is 15~400° C., heating time is 1~600 hours, the mass concentration of acid in the solvent is 0.1~100%.

Yet still another aspect of this invention provides a method for preparing a curing agent of Formula I or II as described above. The method comprises the step of reacting a compound of Formula I-a or II-a with hydrazine. A and B in Formula I-a, and A, B and C in Formula II-a, are the same as those defined above or in the annexed claims for Formulae I and II.

Formula I-a

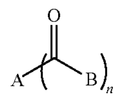

Formula II-a

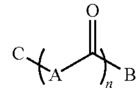

In some embodiments of the methods, the mole ratio of the compound of Formula I-a or the compound of Formula II-a to hydrazine is 1:2~100, and the reaction is conducted at a temperature of −20~150° C.

As used herein, the term "alkyl," when used alone or as part of a larger moiety (e.g., as in "cycloalkenylalkyl"), refers to a saturated aliphatic hydrocarbon group. It can contain 1 to 12 (e.g., 1 to 8, 1 to 6, or 1 to 4) carbon atoms. As a moiety, it can be denoted as $—C_nH_{2n+1}$. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., optionally substituted) with one or more substituents. When an alkyl is preceded by a carbon-number modifier, e.g., $C_{1-8}$, its means the alkyl group contains 1 to 8 carbon atoms.

As used herein, the term "alkylene," when used alone or as part of a larger moiety (e.g., as in "arylalkyleneoxy"), refers to a saturated aliphatic hydrocarbon group with two radical points for forming two covalent bonds with two other moieties. It can contain 1 to 12 (e.g., 1 to 8, 1 to 6, or 1 to 4) carbon atoms. As a moiety, it can be denoted as $—C_nH_{2n}—$. Examples of an alkylene group include, but are not limited to, methylene ($—CH_2—$), ethylene ($—CH_2CH_2—$), and propylene ($—CH_2CH_2CH_2—$). When an alkylene is preceded by a carbon-number modifier, e.g., $C_{2-8}$, it means the alkylene group contains 2 to 8 carbon atoms.

As used herein, the term "alkynyl," when used alone or as part of a larger moiety (e.g., as in "alkynylalkyl"), refers to an aliphatic hydrocarbon group with at least one triple bond. It can contain 2 to 12 (e.g., 2 to 8, 2 to 6, or 2 to 4) carbon atoms. An alkynyl group can be straight or branched. Examples of an alkynyl group include, but are not limited to, propargyl and butynyl. When an alkynyl is preceded by a carbon-number modifier, e.g., $C_{2-8}$, it means the alkynyl group contains 2 to 8 carbon atoms.

As used herein, the term "alkenyl," when used alone or as part of a larger moiety (e.g., as in "alkenylalkyl"), refers to an aliphatic hydrocarbon group with at least one double bond. It can contain 2 to 12 (e.g., 2 to 8, 2 to 6, or 2 to 4) carbon atoms. An alkenyl group with one double bond can be denoted as $—C_nH_{2n-1}$, or $—C_nH_{2n-3}$ with two double bonds. Like an alkyl group, an alkenyl group can be straight or branched. Examples of an alkenyl group include, but are not limited to, allyl, isoprenyl, 2-butenyl, and 2-hexenyl. When an alkylene is preceded by a carbon-number modifier, e.g., $C_{3-8}$, it means the alkylene group contains 3 to 8 carbon atoms.

As used herein, the term "cycloalkyl," when used alone or as part of a larger moiety (e.g., as in "cycloalkylalkyl"), refers to a saturated carbocyclic mono-, bi-, or tri-cyclic (fused or bridged or spiral) ring system. It can contain 3 to 12 (e.g., 3 to 10, or 5 to 10) carbon atoms. Examples of cycloalkyl groups include, but are not limited to, cyclopropyl, cyclobutyl, cyclopentyl, cyclohexyl, cycloheptyl, adamantyl, norbornyl, cubyl, octahydro-indenyl, decahydronaphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl) cycloalkyl. When a cycloalkyl is preceded by a carbon-number modifier, e.g., $C_{3-8}$, its means the alkyl group contains 3 to 8 carbon atoms.

As used herein, the term "cycloalkenyl," when used alone or as part of a larger moiety (e.g., as in "cycloalkenylalkyl"), refers to a non-aromatic carbocyclic ring system having one or more double bonds. It can contain 3 to 12 (e.g., 3 to 10, or 5 to 10) carbon atoms. Examples of cycloalkenyl groups include, but are not limited to, cyclopentenyl, 1,4-cyclo-hexa-di-enyl, cycloheptenyl, cyclooctenyl, hexahydro-indenyl, octahydro-naphthyl, cyclohexenyl, cyclopentenyl, bicyclo[2.2.2]octenyl, orbicyclo[3.3.1]nonenyl.

As used herein, the term "heterocycloalkyl," when used alone or as part of a larger moiety (e.g., as in "heterocycloalkylalkyl"), refers to a 3- to 16-membered mono-, bi-, or tri-cyclic (fused or bridged or spiral)) saturated ring structure, in which one or more of the ring atoms is a heteroatom (e.g., N, O, S, or combinations thereof). In addition to the heteroatom(s), the heterocycloalkyl can contain 3 to 15 carbon atoms (e.g., 3 to 12 or 5 to 10). Examples of a heterocycloalkyl group include, but are not limited to, piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, l-aza-bicyclo[2.2.2]octyl, 3-aza-bicyclo[3.2.1]octyl, and 2,6-dioxa-tricyclo[3.3.1.03,7]nonyl. A monocyclic heterocycloalkyl group can be fused with a phenyl moiety such as tetrahydroisoquinoline. When a heterocycloalkyl is preceded by a carbon-number modifier, e.g., $C_{4-8}$, it means the heterocycloalkyl group contains 4 to 8 carbon atoms.

As used herein, the term "hetero," when used alone or as part of a larger moiety (e.g., as in "heterocyclo," "heterocycloalkyl," "heterocycloalkylene" or "heteroaryl"), refers to a hetero atom or group that is —O—, —S—, —NH—, —C(═O)—, or P.

When being a hetero ring atom, P can take the form of —P—, —P(O)—, $—P(O)_2—$, or $—P(O)_2R—$.

As used herein, the term "aryl," when used alone or as part of a larger moiety (e.g., as in "arylkyl," or "arylkoxy"), refers to a monocyclic (e.g., phenyl), bicyclic (e.g., indenyl, naphthalenyl, or tetrahydronaphthyl), and tricyclic (e.g., fluorenyl, tetrahydrofluorenyl, tetrahydroanthracenyl, or anthracenyl) ring system in which the monocyclic ring system is aromatic (e.g., phenyl) or at least one of the rings in a bicyclic or tricyclic ring system is aromatic (e.g., phenyl). The bicyclic and tricyclic groups include, but are not limited to, benzo-fused 2- or 3-membered carbocyclic rings. For instance, a benzo-fused group includes phenyl fused with two or more $C_{4-8}$ carbocyclic moieties.

As used herein, the term "heteroaryl" refers to a monocyclic, bicyclic, or tricyclic ring system having 5 to 15 ring atoms wherein at least one of the ring atoms is a heteroatom (e.g., N, O, S, or combinations thereof) and when the monocyclic ring system is aromatic or at least one of the rings in the bicyclic or tricyclic ring systems is aromatic. It can contain 5 to 12 or 8 to 10 ring atoms. A heteroaryl group includes, but is not limited to, a benzo-fused ring system having 2 to 3 rings. For example, a benzo-fused group includes benzo fused with one or two 4- to 8-membered heterocycloalkyl moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, IH-indazolyl, furyl, pyrrolyl, thienyl, thiazolyl, oxazolyl, imidazolyl, tetrazolyl, benzofuryl, isoquinolinyl, benzithiazolyl, xanthenyl, thioxanthenyl, phenothiazinyl, dihydroindolyl, benzo[1,3]dioxolyl, benzo [b] furyl, benzo [bjthiophenyl, indazolyl, benzimidazolyl, benzthiazolyl, puryl, quinolinyl, quinazolinyl, phthalazyl, quinazolyl, quinoxalyl, isoquinolinyl, 4H-quinolizyl, benzo-1,2,5-thiadiazolyl, and 1,8-naphthyridyl.

As used herein, the suffix "-ene" is used to describe a bivalent group with two radical points for forming two covalent bonds with two other moieties. In other words, any of the terms as defined above can be modified with the suffix "-ene" to describe a bivalent version of that moiety. For example, a bivalent aryl ring structure is "arylene," a bivalent benzene ring structure is "phenylene," a bivalent heteroaryl ring structure is "heteroarylene," a bivalent cycloalkyl ring structure is a "cycloalkylene," a bivalent heterocycloalkyl ring structure is "heterocycloalkylene," a bivalent cycloalkenyl ring structure is "cycloalkenylene," a bivalent alkenyl chain is "alkenylene," and a bivalent alkynyl chain is "alkynylene."

As used herein, the term "optionally" (e.g., as in "optionally substituted with") means that the moiety at issue is either substituted or not substituted, and that the substitution occurs only when it is chemically feasible. For instance, H cannot be substituted with a substituent and a covalent bond or —C(═O)— group cannot be substituted with a substituent.

As used herein, an "oxo" or "oxide" group refers to ═O.

As used herein, a "carbonyl" group refers to —C(O)— or —C(═O)—.

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

For convenience and as commonly understood, the term "optionally substituted" only applies to the chemical entities that can be substituted with suitable substituents, not to those that cannot be substituted chemically.

As used herein, the term "or" can mean "or" or "and."

DETAILED DESCRIPTION OF THE INVENTION

The following examples are provided for illustration only, and not intended to be limiting in any aspect.

Example 1

Preparation of Curing Agent 1

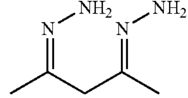

Curing Agent 1

70 g ethanol and 36.7 g 85% hydrazine hydrate were placed in the flask reactor. 25 g 2,4-pentandione dissolved in 40 g ethanol was added dropwise while stirring at the room temperature for one hour. Then the solution was heated to reflux for 5~6 hours. The solution was concentrated at reduced pressure, and then the residue solid was washed with petroleum ether, filtered and dried to give 10 g white solid.

MP: 104~106° C.

$^1$H-NMR ($CDCl_3$, 400 MHz): 2.27 (s, 6H), 5.82 (s, 1H).

Example 2

Preparation of Curing Agent 1

70 g ethanol and 36.7 g 85% hydrazine hydrate were placed in the flask reactor, 25 g 2,4-pentandione dissolved in 40 g ethanol was added dropwise while stirring at the room temperature in one hour, then the solution was heated to 60~65° C. After 5~6 hours, the solution was concentrated at reduced pressure, then the residue solid was washed with petroleum ether, filtered and dried to give 10.7 g white solid.

Example 3

Preparation of Curing Agent 1

70 g ethanol and 36.7 g 85% hydrazine hydrate were placed in the flask reactor. 25 g 2,4-pentandione dissolved in 40 g ethanol was added dropwise while stirring at the room temperature for one hour. Then the solution was heated to 40~45° C. After 5~6 hours, the solution was concentrated, and then the residue solid was washed with petroleum ether, filtered and dried to give 11.5 g white solid.

Example 4

Preparation of Curing Agent 1

70 g ethanol and 36.7 g 85% hydrazine hydrate were placed in the flask reactor. 25 g 2,4-pentandione dissolved in 40 g ethanol was added dropwise while stirring at the room temperature for one hour. Then the solution was heated to the room temperature. After 5-6 hours, the solution was concentrated, and then the residue solid was washed with petroleum ether, filtered and dried to give 13.4 g white solid.

Example 5

Preparation of Curing Agent 1

70 g ethanol and 36.7 g 85% hydrazine hydrate were placed in the flask reactor and cooled to 0~5° C. 25 g 2,4-Pentandione dissolved in 40 g ethanol was added dropwise while stirring at 5~10° C. for one hour. After 5-6 hours below 10° C., the solution was concentrated, and the residue solid was washed with petroleum ether, then filtered and dried to give 15 g white solid.

Example 6

Preparation of Curing Agent 2

Curing Agent 2

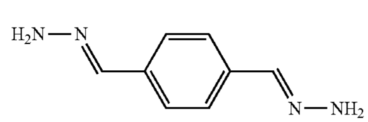

20 g ethanol and 14.7 g 85% hydrazine hydrate were placed in the flask reactor. 13.4 g 1,4-phthalaldehyde dissolved in 370 g ethanol was added dropwise while stirring at the room temperature for one hour. The solution was stirring at the room temperature for 5-6 hours, and then filtered. The filter cake was washed with ethanol and dried to give 13.9 g yellow solid.

MP: 158~166° C.

$^1$H-NMR (400 MHz, $d_6$-DMSO): 7.67 (s, 2H), 7.42 (s, 4H), 6.76 (s, 4H).

Example 7

Preparation of Curing Agent 2

20 g ethanol and 14.7 g 85% hydrazine hydrate were placed in the flask reactor. 13.4 g 1,4-phthalaldehyde dissolved in 370 g ethanol was added dropwise while stirring at the room temperature for one hour. Then the solution was heated to 40~45° C. After 5~6 hours, the solution was cooled to room temperature, filtered, and the filter cake was washed with ethanol and dried to give 13.5 g yellow solid.

Example 8

Preparation of Curing Agent 2

20 g ethanol and 14.7 g 85% hydrazine hydrate were placed in the flask reactor. 13.4 g 1,4-phthalaldehyde dissolved in 370 g ethanol was added dropwise while stirring at the room temperature for one hour. Then the solution was heated to 60~65° C. After 5~6 hours, the solution was cooled to room temperature, filtered, and the filter cake was washed with ethanol and dried to give 11 g yellow solid.

Example 9

Preparation of Curing Agent 2

20 g ethanol and 14.7 g 85% hydrazine hydrate were placed in the flask reactor. 13.4 g 1,4-phthalaldehyde dissolved in 370 g ethanol was added dropwise while stirring at the room temperature for one hour. Then the solution was heated to reflux for 5~6 hours, the solution was cooled to the room temperature, filtered, and the filter cake was washed with ethanol and dried to give 10.3 g yellow solid.

Example 10

Preparation of Curing Agent 2

20 g ethanol and 14.7 g 85% hydrazine hydrate were placed in the flask reactor and cooled to 0~5° C., 13.4 g 1,4-phthalaldehyde dissolved in 370 g ethanol was added dropwise while stirring at 5~10° C. for one hour. After 5-6 hours below 10° C., and the solution was cooled to the temperature, filtered, the filter cake was washed with ethanol and dried to give 14.6 g yellow solid.

Example 11

Preparation of Curing Agent 3

Curing Agent 3

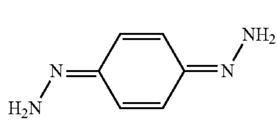

20 g ethanol and 14.7 g 85% hydrazine hydrate were placed in the flask reactor and cooled to 0~5° C., 10.8 g 1,4-benzoquinone dissolved in 180 g ethanol was added dropwise while stirring at 5~10° C. for one hour. The reaction was heated to reflux for 5-6 hours, the solution was concentrated at reduced pressure, and the filter cake was washed with ethanol, filtered and dried to give 8.4 g brown solid.

MP: 140~142° C.

$^1$H-NMR (400 MHz, $d_6$-DMSO): 6.56 (s, 4H), 5.52 (s, 4H).

Example 12

Preparation of Curing Agent 3

20 g ethanol and 14.7 g 85% hydrazine hydrate were placed in the flask reactor and cooled to 0~5° C., 10.8 g 1,4-benzoquinone dissolved in 180 g ethanol was added dropwise while stirring at 5~10° C. for one hour. The reaction was heated to 60~65° C. After 5-6 hours, the solution was concentrated at reduced pressure, and the solid was washed with ethanol, filtered and dried to give 9.4 g brown solid.

Example 13

Preparation of Curing Agent 3

20 g ethanol and 14.7 g 85% hydrazine hydrate were placed in the flask reactor and cooled to 0~5° C., 10.8 g 1,4-benzoquinone dissolved in 180 g ethanol was added dropwise while stirring at 5~10° C. for one hour. The reaction was heated to 40~45° C. After 5-6 hours, the solution was concentrated at reduced pressure, the solid was washed with ethanol, filtered and dried to give 10.2 g brown solid.

Example 14

Preparation of Curing Agent 3

20 g ethanol and 14.7 g 85% hydrazine hydrate were placed in the flask reactor and cooled to 0~5° C., 10.8 g 1,4-benzoquinone dissolved in 180 g ethanol was added dropwise while stirring at 5~10° C. for one hour. The reaction was heated to room temperature. After 5-6 hours, the solution was concentrated at reduced pressure, the solid was washed with ethanol, filtered and dried to give 11.0 g brown solid.

Example 15

Preparation of Curing Agent 3

20 g ethanol and 14.7 g 85% hydrazine hydrate were placed in the flask reactor and cooled to 0~5° C., 10.8 g 1,4-benzoquinone dissolved in 180 g ethanol was added dropwise while stirring at 5~10° C. for one hour. After 5~6 hours below 10° C., and the solution was concentrated at reduced pressure, and the solid was washed with ethanol, filtered and dried to give 11.8 g brown solid.

Example 16

Preparation of Curing Agent 4

Curing Agent 4

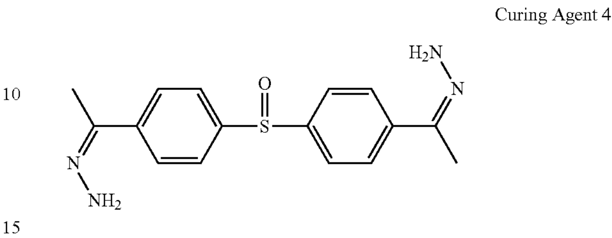

Step 1: To a flask, 250 mL of dichloroethane and aluminum chloride (62.64 g, 0.47 mol) was added. Acetyl chloride (31.58 g, 0.40 mol) was added slowly to this mixture at 10° C. and followed by phenyl sulfide (25 g, 0.13 mol). After addition, temperature was increase to room temperature and stirred for 8 h. The reaction was quenched by poured to 500 mL of crushed ice, the organic layer was extracted with chloroform, and the combined organic layers were washed with a saturated sodium bicarbonate, followed by a saturated brine solution and dried over anhydrous sodium sulfate and evaporated at vacuum to give compound 2 28 g (yield=80%).

$^1$H-NMR ($CDCl_3$, 400 MHz) δ 2.57 (6H, s), 7.40 (4H, d), 7.90 (4H, d)

Step 2: To a 500 mL three-necked flask, 18.66 g (0.069 mole) of bis(4-acetylphenyl)sulfide, 180 g of acetic acid and 40 g of dichloroethane were fed. To the resulting solution, 0.54 g (0.001 mole) of 20 percent aqueous solution of titanium trichloride was added, and 6.21 g (0.054 mole) of 30 percent aqueous hydrogen peroxide solution was added thereto dropwise, followed by stirring the resulting mixture for 2 hours. To this mixture, 300 mL of water was added, dichloroethane was evaporated and the resulting mixture was cooled to 10° C., followed by collection of yielded crystals by filtration. These crystals were washed with 90 mL of methanol and collected by filtration, purified by column chromatography on silica gel (petroleum/ethyl acetate=4:1 to 2:1) to provide the desired product 3 3.6 g. The yield was 19%.

$^1$H-NMR ($CDCl_3$, 400 MHz) δ 2.60 (6H, s), 7.78 (4H, d), 8.05 (4H, d)

Step 3: To a 50 mL three-necked flask, 1.7 mL of 85% hydrazine hydrate, 15 mL of ethanol were fed. To the resulting solution, 1.6 g (0.006 mole) of product 3 was added partially and stirred at room temperature overnight. The precipitation was collected by filtration and dried thereof to obtain product 41.2 g. The yield was 64%.

$^1$H-NMR ($CDCl_3$, 400 MHz): δ 2.11 (6H, s), 5.46 (4H, s) 7.60 (4H, d), 7.72 (4H, d).

MP (from DSC): 161.89° C.

Example 17

Preparation of Cured Degradable Epoxy Matrix 10 g Curing Agent 1 in Example 1 (AEW≈3.1 N—H eq./100 g) and 58.9 g liquid bisphenol A epoxy resin of E52D (EEW 0.52~0.54 eq./100 g) were mixed and stirred evenly at the room temperature. Under 70° C. conditions, the gel time of resin mixture was more than 4 hours, and half time of the resin mixture was more than a month at room temperature. Appropriate amount of the resin mixture was painted on a glass slide, heated to 125° C. for 2 hours until fully cured to give the sample of cured degradable epoxy resin.

Example 18

Preparation of Cured Degradable Epoxy Matrix 10 g Curing Agent 2 in Example 6 (AEW≈2.47 N—H eq./100 g) and 46.4 g liquid bisphenol A epoxy resin of E52D (EEW 0.52~0.54 eq./100 g) were mixed and stirred evenly at the room temperature. Under 70° C. conditions, the gel time of resin mixture was more than 4 hours, and half time of the resin mixture was more than a month at room temperature. Appropriate amount of the resin mixture was painted on a glass slide, heated to 120° C. for 2 hours until fully cured to give the sample of cured degradable epoxy resin.

Example 19

Preparation of Cured Degradable Epoxy Matrix 10 g Curing Agent 3 in Example 11 (AEW≈2.94 H eq./100 g) and 55.4 g liquid bisphenol F epoxy resin (EEW 0.5~0.63 eq./100 g) were mixed and stirred evenly at the room temperature. Under 70° C. conditions, the gel time of resin mixture was more than 4 hours, and half time of the resin mixture was more than a month at room temperature. Appropriate amount of the resin mixture was painted on a glass slide, heated to 70° C. for 2 hours, 125° C. for 2 hours and then 160° C. for 2 hours until fully cured to give the sample of cured degradable epoxy resin.

Example 20

Preparation of Cured Degradable Epoxy Matrix 2.36 g bisphenol A epoxy resin NPEL128 (EEW 0.52~0.54 eq./100 g) and 1.0 g curing agent 4 (AEW≈1.27 H eq./100 g) in example 16 were mixed and stirred evenly at the room temperature, and then the mixture was heated at 130° C. for 4 hours to obtain the cured degradable epoxy resin sample.

Example 21

Degradation of Cured Degradable Epoxy Matrix 0.5 g of the cured sample in Example 17, 10 mL concentrated hydrochloric acid, and 90 mL ethylene glycol were placed in a one-neck round flask, stirred and heated to 180° C., completely degraded after 10 hours to give transparent clear solution, which was neutralized with 20% sodium hydroxide solution and then precipitated solid was filtered, and the solid was washed with water and dried to give 0.48 g of degradation products of thermoset epoxy resin, mass recovery ratio was 96%.

Example 22

Degradation of Cured Degradable Epoxy Matrix 0.40 g of the cured sample in Example 18, 5 mL concentrated hydrochloric acid, and 90 ml ethylene glycol were placed in an autoclave, stirred and heated to 160° C., completely degraded after 15 hours to give transparent clear solution, which was neutralized with 20% sodium hydroxide solution and then precipitated solid was filtered, and the solid was washed with water and dried to give 0.38 g of degradation products of thermoset epoxy resin, mass recovery ratio was 95%.

Example 23

Degradation of Cured Degradable Epoxy Matrix 0.6 g of the cured sample in Example 19, 10 mL concentrated hydrochloric acid, and 90 ml ethylene glycol were placed in a one-neck round flask, stirred and heated to 150° C., completely degraded after 20 hours and transparent clear solution was obtained, which was neutralized with 20% sodium hydroxide solution and precipitated solid was filtered and the solid was washed with water and dried to give 0.58 g of degradation products of thermoset epoxy resin, mass recovery ratio was 96.6%.

Example 24

Degradation of Cured Degradable Epoxy Matrix 0.3 g cured sample in example 20, 2.5 mL concentrated hydrochloric acid and 50 mL ethylene glycol were placed in a 100 ml three-neck flask, stirred and heated to 155° C., completely degraded after 2 hours, and brown transparent solution was obtained, which was neutralized with 20% sodium hydroxide solution and precipitated solid was filtered and the solid was washed with water and dried to give 0.29 g of degradation products of thermoset epoxy resin, mass recovery ratio was 96.7%.

Example 25

Preparation and Properties of Degradable Epoxy Matrix 20 g bisphenol A epoxy resin NPEL-128 (EEW 0.52~0.54 eq./100 g) and 11 g Curing Agent 2 in Example 6 (AEW 2.47 N—H eq./100 g), 20 g CTBN (Carboxyl terminated butadiene acrylonitrile rubber) modified epoxy (EEW 0.267~0.308 eq./100 g) and 26 g MDI modified epoxy resin (EEW 0.33 eq./100 g) were mixed in a high speed blender at 70° C. 30 minutes, discharged, and cooled to room temperature, then frozen for storage. The curing cycle for the resultant degradable epoxy system is 100° C. for 1 hour followed by 125° C. for 2 hours The typical properties of the resultant degradable epoxy system are listed in the below table.

| | |
|---|---|
| Viscosity @ 70 ± 1° C. (cps) | 7800 |
| Gel time @ 115° C. (min) | 35~40 |
| Density (g/cm$^3$) | 1.2~1.25 |
| Viscosity doubling time (hrs, 20 g@70 ± 1° C.) | >4 |
| Tg (Cure Cycle: 100° C. × 1 h + 125° C. × 2 h) | 141~147° C. |
| Flexural strength (MPa) | 109~119 |
| Flexural modulus (GPa) | 2.0~2.2 |
| Tensile strength (MPa) | 45~55 |
| Tensile modulus (GPa) | 2.1~2.3 |
| Elongation (%) | 2.1~3.0 |

Example 26

Degradation of Cured Degradable Epoxy Matrix 10 g cured sample of degradable epoxy system in Example 25, 20 mL concentrated hydrochloric acid and 190 mL ethylene glycol were placed in a 500-mL three-neck flask, stirred and heated to 155° C., completely degraded after 48 hour, and brown transparent solution was obtained, the solution was neutralized with 70% sodium hydroxide solution and precipitated solid was filtered and the solid was washed with water and dried to give 9.6 g of degradation products of epoxy resin, mass recovery ratio was 96%.

Example 27

Preparation of Degradable Epoxy Carbon Fiber Prepregs 1000 g degradable epoxy system in Example 25 was loaded onto a resin film making machine and heated up to 70° C., then melted. The temperature of the rubber roller was set to 70° C., then the resin film making machine was switched on to produce adhesive film, and the film surface density was 75 $g/m^2$. The prepreg preparation equipment was activated to adjust the carbon fiber surface density to be 100 $g/m^2$. The prepared epoxy resin film was put into the prepreg preparation equipment to compound with carbon fibers to prepare the prepregs, the compound temperature was 95° C. and compound speed was 9 m/min.

Example 28

Preparation for Degradable Epoxy Resin Laminated Sheets

A mould was placed on a hot-pressing machine, then heated up to 100° C. for standby application. The prepared prepregs in Example 27 were trimmed to the size of 300 mm×300 mm, then 22 layers of prepreg materials were laid in the mould with the same direction. The prepreg materials were clamped and pressured to prepare the composite laminated sheets. Its parameter of preparation process was as follows: 0.5 MPa pressure and 100° C. for 1 hour followed by 125° C. for 2 hours. The heating electric power was switched off to naturally cool the composite laminated sheets down to a temperature below 50° C., then the prepared composite laminated sheets were removed from the mould. The mechanical properties of the composite laminate sheets prepared by this specific embodiment were as follows:

| Carbon Fiber Laminates | Unit | Mean | Normalized | Standard |
|---|---|---|---|---|
| Carbon Fiber Content | % | 50.3 | 60 | n/a |
| Tensile Strength | MPa | 1250 | 1491 | GB3354 |
| Tensile Modulus | GPa | 111.8 | 133.4 | GB3354 |
| Elongation | % | 0.43 | n/a | GB3354 |
| Flexural Strength | MPa | 1154.48 | 1377.11 | GB3356 |
| Flexural Modulus | GPa | 101.1 | 120.6 | GB3356 |
| Compression Strength | MPa | 500.5 | 597 | GB3856 |
| Compression Modulus | GPa | 102.2 | 122 | GB3856 |
| ILSS | MPa | 41.84 | 49.9 | JC773 |
| IPSS | MPa | 77.63 | n/a | GB3355 |
| IPSM | GPa | 4.5 | n/a | GB3355 |

Example 29

Degradation of Degradable Carbon Fiber Reinforced Composite 1 g sample of the carbon fiber composite laminate in Example 28 (49.7% resin content), 5 mL concentrated hydrochloric acid and 95 mL ethylene glycol were placed in a 250 mL three-neck flask, stirred and heated to 155° C., completely degraded after 48 hours, filtered. The carbon fiber and the degradation solution were separated, the solution was neutralized with 70% sodium hydroxide solution to give a precipitated solid. The solid was filtered and washed with water, dried to give 0.48 g degraded epoxy resin, mass recovery ratio was 96%.

Example 30

Degradation of the Carbon Fiber Fishing Rod

One end of a fishing rod made from degradable carbon fiber prepreg in Example 27 was submerged in a mixture of 10 mL concentrated hydrochloric acid and 190 mL ethylene glycol, heated to 155° C. After 48 hours, the treated end of the fishing rod was washed with water and dried. The immersed part of the rod became disintegrated and remained only in the form of loose carbon fibers. This result confirmed the prepreg materials of this invention could be degraded under the conditions described above.

Other Embodiments of the Invention

The invention has been described above with the reference to specific examples and embodiments, not to be constructed as limiting the scope of this invention in any way. It is understood that various modifications and additions can be made to the specific examples and embodiments disclosed without departing from the spirit of the invention, and such modifications and additions are contemplated as being part of the present invention.

What is claimed is:

1. A degradable cross-linked polymer comprising a cleavable cross-linking group derived from a curing agent and an epoxy resin, wherein the cleavable cross-linking group is derived from

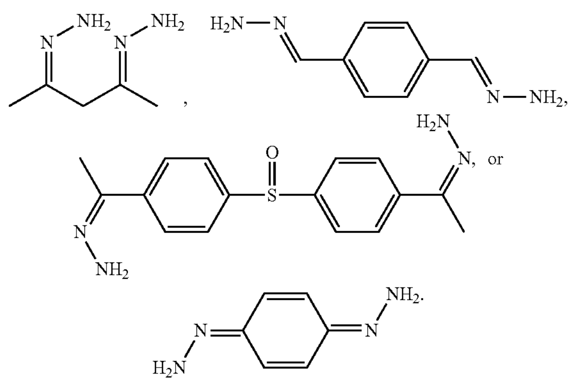

and at least one amino group of which is fully reacted to lose both hydrogen atoms.

2. A method for degrading a degradable cross-linked polymer of claim 1, comprising the steps of:

(1) under the heating and stirring conditions, immersing the polymer in a mixed acid and solvent system to obtain a degradation solution; and (2) using an alkaline solution to control the pH of the degradation solution.

3. The method of claim 2, further comprising a step of washing and drying the precipitate and degradation solution after pH adjustment in step (2).

4. The method of claim 2, wherein the acid comprises a hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid; the alkali comprises lithium hydroxide, sodium hydroxide, potassium hydroxide, calcium hydroxide, sodium carbonate, sodium bicarbonate, potassium carbonate, potassium bicarbonate, or ammonia; each of the solvent for immersing the polymer in step (1) and the solvent for the alkaline solution in step (2) independently comprises methanol, ethanol, ethylene glycol, propanol, isopropanol, butanol, isobutanol, t-butanol, pentanol, hexanol, heptanol, octanol, nonanol, benzyl alcohol, phenethyl alcohol, p-hydroxymethyl benzene, m-hydroxymethyl benzene, o-hydroxy benzene, p-hydroxyethyl benzene, m-hydroxyethyl benzene, o-hydroxyethyl benzene, water, N, N-dimethylformamide, N, N-dimethylacetamide, N-methylpyrrolidone, dimethyl sulfoxide, tetrahydrofuran, methyl tetrahydrofuran, glycerol, or dioxane.

5. The method of claim 2, wherein in step (1), the heating temperature is in the range of 80~150° C., and the heating time is 4~8 hours, and the mass concentration of the acid in the solvent system is 0.5~20% (w/w); and in step (2), the temperature is in the range of 5~50° C., the final pH is 6~12, and the mass concentration of the alkali in the solvent is 5~30% (w/w).

* * * * *